(12) United States Patent
Boden et al.

(10) Patent No.: US 9,631,042 B2
(45) Date of Patent: *Apr. 25, 2017

(54) COPOLYMERS HAVING POLYISOBUTYLENE AND BIODEGRADABLE POLYMER SEGMENTS

(71) Applicants: Boston Scientific Scimed, Inc., Maple Grove, MN (US); University of Massachusetts Lowell, Lowell, MA (US)

(72) Inventors: Mark Boden, Harrisville, RI (US); Marlene C. Schwarz, Auburndale, MA (US); Frederick H. Strickler, Natick, MA (US); Rudolf Faust, Lexington, MA (US); Umaprasana Ojha, Lowell, MA (US); Tomoya Higashihara, Tokyo (JP)

(73) Assignees: BOSTON SCIENTIFIC SCIMED, INC., Maple Grove, MN (US); THE UNIVERSITY OF MASSACHUSETTS LOWELL, Lowell, MA (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/539,449

(22) Filed: Nov. 12, 2014

(65) Prior Publication Data

US 2015/0203622 A1 Jul. 23, 2015

Related U.S. Application Data

(63) Continuation of application No. 12/650,234, filed on Dec. 30, 2009, now Pat. No. 8,911,760.

(Continued)

(51) Int. Cl.
| | | |
|---|---|---|
| C08F 299/04 | (2006.01) | |
| A61L 27/16 | (2006.01) | |
| A61L 27/54 | (2006.01) | |
| A61L 27/58 | (2006.01) | |
| A61L 29/04 | (2006.01) | |
| A61L 29/14 | (2006.01) | |
| A61L 29/16 | (2006.01) | |
| A61L 31/04 | (2006.01) | |
| A61L 31/14 | (2006.01) | |
| A61L 31/16 | (2006.01) | |

(Continued)

(52) U.S. Cl.
CPC .......... *C08F 299/04* (2013.01); *A61L 27/165* (2013.01); *A61L 27/54* (2013.01); *A61L 27/58* (2013.01); *A61L 29/041* (2013.01); *A61L 29/148* (2013.01); *A61L 29/16* (2013.01); *A61L 31/048* (2013.01); *A61L 31/148* (2013.01); *A61L 31/16* (2013.01); *C08G 18/4266* (2013.01); *C08G 18/6204* (2013.01); *C08G 18/7671* (2013.01); *C08G 63/00* (2013.01); *C08G 63/06* (2013.01); *C08G 63/912* (2013.01); *C08G 64/18* (2013.01); *C08G 64/42* (2013.01); *C08G 69/08* (2013.01); *A61L 2300/00* (2013.01); *C08G 2261/126* (2013.01)

(58) Field of Classification Search
CPC ............ C08G 18/4266; C08G 18/6204; C08G 18/7671; C08G 63/00; C08G 63/06; C08G 63/912; C08G 64/18; C08G 64/42; C08G 69/08; C08G 2261/126; C08L 53/02; C08F 299/04; A61L 27/165; A61L 27/58; A61L 27/54; A61L 29/041; A61L 29/148; A61L 29/16; A61L 31/048; A61L 31/148; A61L 31/16; A61L 2300/00
See application file for complete search history.

(56) References Cited

U.S. PATENT DOCUMENTS

| 4,994,526 A | 2/1991 | Peters |
| 6,545,097 B2 | 4/2003 | Pinchuk et al. |

(Continued)

FOREIGN PATENT DOCUMENTS

| JP | 11131325 | 5/1999 |
| WO | 2006083904 A2 | 8/2006 |

(Continued)

OTHER PUBLICATIONS

Sipos et al. ("Synthesis of poly(L-lactide)-block-polyisobutylene-block-poly(L-lactide), a new biodegradable thermoplastic elastomer," in Macromol, Rapid Commun. 16, 935-940 (1995).*
Magenau et al. "Polyisobutylene RAFT CTA by a Click Chemistry Site Transformation Approach: Synthesis of Poly(isobutylene-b-N-isopropylacrylamide)" in Macromolecules, 2009, 42 (21), pp. 4044-8051.*
All non-patent literature documents and foreign documents have been previously uploaded in parent U.S. Appl. No. 12/650,234, filed Dec. 30, 2009.
Tomoya et al. (Synthesis of Novel Block Copolymers Comprised of Polyisobutylene and Poly(vinylferrocene) Segments in Macromolecules 2007, 40, 7453-7463).
Aliferis et al., "Living Polypeptides," Biomacromolecules, 5(2004), 1653-1656.
Binder et al., "Connecting polymetric fragments by Sharpless-type 'click'—reactions," Polym. Prepr. (Am. Chem. Soc., Div. Polym. Chem.) 45(2004) 692-693.

(Continued)

*Primary Examiner* — Blessing M Fubara
(74) *Attorney, Agent, or Firm* — Seager, Tufte & Wickhem, LLP

(57) ABSTRACT

The present invention pertains to copolymers having one or more polyisobutylene segments and one or more biodegradable polymer segments, to methods of making such copolymers, to medical articles that contain such copolymers, and to methods of making such medical articles. According to certain aspects of the invention, copolymers are provided, which comprise a plurality of polyisobutylene segments and a plurality of biodegradable polymer segments. According to certain aspects of the invention, copolymers are provided, which comprise urethane linkages, urea linkages, amide linkages, ester linkages, anhydride linkages, carbonate linkages, linkages commonly described as "click" chemistry linkages, and combinations of two or more types of such linkages.

14 Claims, No Drawings

Related U.S. Application Data

(60) Provisional application No. 61/142,019, filed on Dec. 31, 2008.

(51) Int. Cl.

| | |
|---|---|
| C08G 18/42 | (2006.01) |
| C08G 18/62 | (2006.01) |
| C08G 18/76 | (2006.01) |
| C08G 63/00 | (2006.01) |
| C08G 63/91 | (2006.01) |
| C08G 63/06 | (2006.01) |
| C08G 64/18 | (2006.01) |
| C08G 64/42 | (2006.01) |
| C08G 69/08 | (2006.01) |

(56) References Cited

U.S. PATENT DOCUMENTS

| | | | |
|---|---|---|---|
| 8,911,760 B2* | 12/2014 | Boden | A61L 27/165 424/422 |
| 2001/0049415 A1 | 12/2001 | Kim et al. | |
| 2006/0171985 A1* | 8/2006 | Richard | A61L 27/48 424/423 |
| 2009/0326077 A1 | 12/2009 | Desai et al. | |

FOREIGN PATENT DOCUMENTS

| | | |
|---|---|---|
| WO | 2008066914 A1 | 6/2008 |
| WO | 2009158600 A1 | 12/2009 |

OTHER PUBLICATIONS

Cohn et al., "Briodegradable multiblock. PEO/PLA thermoplastic elastomers: molecular design and properties," A. Polymer 46 (2005) 2068-2075.
Cooper et al., "Poly(lactic Acid) and Chain-Extended Poly(lactic acid)-Polyurethane Functionalized with Pendent Carboxylic Acid Groups," Macromolecules 41 (2008) 655-662.
Dimitrov et al., "Synthesis of nearly monodisperse polystyrene-polypeptide block copolymers via polymerisation of N-carboxyanhydrides." Chem. Commun. 23 (2003) 2944-2945.
Faust et al., "Sytnthesis and Characterization of Novel Biostable Polyisobutylene Based Thermoplastic Polyurethanes," Abstract of Oral Presentation given at 19th IUPAC International Symposium on Ionic Polymerization 2009, Jul. 26-31, 2009, Krakow, Poland.
Frick, et al., "Characterization of Polylactide-b-polyisoprene-b-polylactide Thermoplastic Elastomers," Biomacromolecules 4 (2003) 216-223.
Hamley, "Nanotechnology with Soft Materials," Angew. Chem., Int. Ed. 42 (2003) 1692-1712.
Higashihara et al., "Synthesis of novel ABA triblock and (ABA)n multiblock copolymers comprised of polyisobutylene and poly(y-benzyl-L-glutamate) segments," Reactive and Functional Polymers, 69 (2009) 429-434.
Ibarbourne et al., "Thermotropic Liquid Crystal Behavior on PBLG-PDMS-PBLG Triblock Copolymers," J. Polym. Sci. Part A: Polym. Chem. 44 (2006) 4668-4679.
Kennedy et al., "Designed Polymers by Carbocationic Macromolecular Engineering: Theory and Practice," Hanser Publishers 1991, pp. 191-193, 226-233.
Kennedy, "Synthesis, Characterization and Properties of Polyisobutylene-Based Polyurethanes," Journal of Elastomers and Plastics 17 (1985) 82-88.
Kolb et al., "Click Chemistry: Diverse Chemical Function from a Few Good Reactions," Angew. Chem. Int. Ed. 40 (2001) 2004-2021.
Lee et al., "Modeling of polyethylene and poly ,, L-lactide polymer blends and diblock copolymer: Chain length and volume fraction effects on structural arrangement," J. Chem. Phys. 127 (2007) 064902/1-064902/11.
Nakajima et al., Synthesis and Structural Study of the A-B-A Type Block Copolymer Consisting of Poly(y-benzyl L-glutamate) as the A Component and Polybutadiene as the B Component, Macromolecules 12 (1979) 840-843.
Nakayama et al., "Synthesis of poly(ester-urethane)s from hydroxytelechelic polylactide: Effect of initiators on their physical and degradation properties," Polym. Degrad. Stabil.93 (2008) 117-124.
Ojha et al., "A New General Methodology for the Syntheses of End-Functional Polyisobutylenes by Nucleophilic Substitution Reactions" Macromolecules 41 (2008) 3832-3841.
Ojha et al., "Syntheses and characterization of novel biostable polyisobutylene based thermoplastic polyurethanes" Polymer 50 (2009) 3448-3457.
Ojha et al., "Syntheses, characterization, and properties of multiblock copolymers consisting of polyisobutylene and poly(L-lactide) segments," Journal of Polymer Science Part A: Polymer Chemistry 47 (2009) 3490-3505.
Ojha et al., "Synthesis and Characterization of End-Functionalized Polyisobutylenes for Sharpless-Type Click Reactions," Polymer Preprints 48 (2007) 786-787.
Rajkhowa et al., "Efficient Syntheses of Hydroxyallyl End Functional Polyisobutylenes, A Precursor to Thermoplastic Polyurethanes," Polymer Preprints 48 (2007) 233.
Renade et al., "Styrenic Block Copolymers for biomaterial and drug delivery applications," Acta Biomater: 1 (2005) 137-144.
Sakurai et al., "Mechanical properties of polystyrene-block-polybutadiene-blockpolystyrene triblock copolymers crosslinked in the disordered state," Polymer 40 (1999) 2071-2076.
Sipos et al., "Synthesis of poly(L-lactide)-block-polyisobutylene-block-poly(L-lactide), a new biodegradable thermoplastic elastomer" Macromol. Rapid Commun. 16 (1995) 935-940.
Speckhard et al., "Properties of polyisobutylene polyurethane block copolymers: 2. Macroglycols produced by the "inifer" technique," Polymer 26 (19858) 55-78.
Wang et al., "Polylactide-based polyurethane and its shape-memory behavior," Polym. J. 42 (2006) 1240-1249.
Wang et al., "Shape memory effect of poly(L-lactide)-based polyurethanes with different hard segments," Polym. Int. 56 (2007) 840-846.
Borda et al., "New potentially biodegradable polyurethanes", Polym. Adv. Technol. 2006, 17: 945-953.
T. Higashihara et al., "Synthesis of novel ABA triblock and (ABA)n multiblock copolymers comprised of polyisobutylene and poly(y-benzyl-L-glutamate) segments," Reactive and Functional Polymers, vol. 69, Issue 7, Jul. 2009. pp. 429-434, designated available online Dec. 13, 2008, Elsevier Ltd., UK.

* cited by examiner

COPOLYMERS HAVING POLYISOBUTYLENE AND BIODEGRADABLE POLYMER SEGMENTS

RELATED APPLICATIONS

This application claims priority from U.S. provisional application 61/142,019, filed Dec. 31, 2008, which is incorporated by reference herein in its entirety.

FIELD OF THE INVENTION

The present invention relates, among other things, to copolymers having polyisobutylene and biodegradable polymer segments, to methods of making such copolymers, to medical articles that contain such copolymers, and to methods of making such medical articles.

BACKGROUND OF THE INVENTION

Copolymers are an important class of polymers and have numerous commercial applications. Their unique properties have lead to their use in a wide range of medical products. As one example (among many others), drug eluting stents are known which have polymeric coatings over the stent to release a drug to counteract the effects of in-stent restenosis. Specific examples of drug eluting coronary stents include commercially available stents from Boston Scientific Corp. (TAXUS, PROMUS), Johnson & Johnson (CYPHER), and others. Various types of polymeric materials have been used in such polymeric coatings including, for example, homopolymers such as poly(n-butyl methacrylate) and poly(d,l-lactic acid) and copolymers such as poly(lactic acid-co-glycolic acid), poly(ethylene-co-vinyl acetate), poly(vinylidene fluoride-co-hexafluoropropylene), and poly(isobutylene-co-styrene). Poly(styrene-b-isobutylene-b-styrene) triblock copolymers (SIBS) are described, for instance, in U.S. Pat. No. 6,545,097 to Pinchuk et al. See also S. V. Ranade et al., Acta Biomater. 2005 January; 1(1):137-44. SIBS triblock copolymers have a soft, elastomeric low glass transition temperature (Tg) polyisobutylene midblock and hard elevated Tg polystyrene endblocks. Consequently, SIBS copolymers are thermoplastic elastomers, in other words, elastomeric (i.e., reversibly deformable) polymers that form physical crosslinks which can be reversed, for example, by melting the polymer, by heating it above its glass transition temperature, or by dissolving the polymer in a suitable solvent. SIBS is also highly biocompatible.

SUMMARY OF THE INVENTION

The present invention pertains to copolymers having one or more polyisobutylene (PIB) segments and one or more biodegradable polymer segments, to methods of making such copolymers, to medical articles that contain such copolymers, and to methods of making such medical articles.

According to certain aspects of the invention, copolymers are provided, which comprise a plurality of polyisobutylene segments and a plurality of biodegradable polymer segments.

According to certain aspects of the invention, copolymers containing one or more urethane linkages, urea linkages, amide linkages, ester linkages, anhydride linkages, carbonate linkages, linkages commonly described as "click" chemistry linkages, and combinations of two or more types of such linkages are provided.

These and other aspects and embodiments as well as various advantages of the present invention will become readily apparent to those of ordinary skill in the art upon review of the Detailed Description and any Claims to follow.

DETAILED DESCRIPTION OF THE INVENTION

A more complete understanding of the present invention is available by reference to the following detailed description of numerous aspects and embodiments of the invention. The detailed description of the invention which follows is intended to illustrate but not limit the invention.

As is well known, "polymers" are molecules containing multiple copies (e.g., from 2 to 5 to 10 to 25 to 50 to 100 to 250 to 500 to 1000 or more copies) of one or more constitutional units, commonly referred to as monomers. As used herein, the term "monomers" may refer to free monomers and to those that have been incorporated into polymers, with the distinction being clear from the context in which the term is used.

Polymers may take on a number of configurations, including linear, cyclic and branched configurations, among others. Branched configurations include star-shaped configurations (e.g., configurations in which three or more chains emanate from a hub region), comb configurations (e.g., configurations having a main chain and a plurality of side chains, also referred to as "graft" configurations), dendritic configurations (e.g., arborescent and hyperbranched polymers), and so forth.

As used herein, "homopolymers" are polymers that contain multiple copies of a single constitutional unit (i.e., monomer), whereas "copolymers" are polymers that contain multiple copies of at least two dissimilar constitutional units.

As used herein, a "polymeric segment" or "segment" is a portion of a polymer.

Copolymers in accordance with the invention may include, for example, the following segments: polyisobutylene segments, biodegradable polymer segments, and optional chain extender residues, among others. Segments can be unbranched or branched. Segments can contain a single type of constitutional unit (also referred to herein as "homopolymeric segments") or multiple types of constitutional units (also referred to herein as "copolymeric segments") which may be present, for example, in a random, statistical, gradient, or periodic (e.g., alternating) distribution, among others.

As used herein, a soft segment is one that displays a glass transition temperature ($T_g$) and/or melting temperature ($T_m$) that is below body temperature, more typically from 35° C. to 20° C. to 0° C. to −25° C. to −50° C. or below. A hard segment is one that displays a $T_g$ and/or $T_m$ that is above body temperature, more typically from 40° C. to 50° C. to 75° C. to 100° C. or above. $T_g$ and $T_m$ can be measured by differential scanning calorimetry (DSC), dynamic mechanical analysis (DMA) or thermomechanical analysis (TMA).

In various embodiments, the copolymers of the present invention are fully biodisintegrable. In these embodiments, the molecular weight of the polyisobutylene segments is selected to be low enough to allow for the eventual disintegration of the copolymer in vivo. This molecular weight will vary depending in vivo location of the polymer, and can be determined by those of ordinary skill in the art.

Copolymers in accordance with the invention include at least one soft polyisobutylene segment, and may optionally include one or more additional soft segments (e.g., one or more soft biodegradable polymeric segments and/or one or more soft chain extender residues, among others.). Copolymers in accordance with the invention may also include zero, one or more hard segments (e.g., one or more hard biodegradable segments and/or one or more hard chain extender residues, such hard diisocyanate residues, among others).

Typically, copolymers in accordance with the present invention comprise from 1 to 99 wt % polyisobutylene segments (e.g., from 1 to 2 to 5 to 10 to 25 to 50 to 75 to 90 to 95 to 98 to 99 wt % polyisobutylene segments) and from 1 to 99 wt % biodegradable segments (e.g., from 1 to 2 to 5 to 10 to 25 to 50 to 75 to 90 to 95 to 98 to 99 wt % biodegradable segments).

In certain embodiments, a hard biodegradable segment (e.g., polylactide, etc.) is employed, in which case the copolymer may be provided with an amount of polyisobutylene that is sufficient to allow the copolymer to be flexed or expanded without cracking. One example of a medical article where such a copolymer may be employed is a vascular stent. By providing a sufficient amount of the polyisobutylene in the copolymer, the stent may be expanded without cracking.

Polyurethanes are a family of copolymers that comprise urethane linkages,

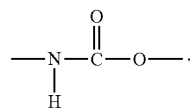

They may be synthesized from (a) mono- and poly-functional isocyanates, which may be monomeric or polymeric in nature and (b) mono- and poly-functional alcohols, which may be monomeric or polymeric in nature.

Specific examples of monofunctional and multifunctional monomeric isocyanates include aliphatic and aromatic diisocyanates such as those set forth below, among many others. Specific examples of monofunctional and multifunctional polymeric isocyanates include (a) mono-, di- and tri-functional isocyanates having at least one polyisobutylene segment, (b) mono-, di- and tri-functional isocyanates having at least one biodegradable polymeric segment (e.g., biodegradable polyester, polycarbonate, polyorthoester, polyanhydride, poly-amino-acid and/or polyphosphazine segments, among others), and (c) mono-, di- and tri-functional isocyanates having at least one polyisobutylene segment and at least one biodegradable polymeric segment.

Specific examples of monofunctional and multifunctional monomeric alcohols include aliphatic and aromatic polyols, for instance, including the diols set forth hereinbelow, among many others. Specific examples of monofunctional and multifunctional polymeric alcohols include (a) mono-, di- and tri-functional alcohols having at least one polyisobutylene segment, (b) mono-, di- and tri-functional alcohols comprising at least one biodegradable polymeric segment (e.g., biodegradable polyester, polycarbonate, polyorthoester, polyanhydride, poly-amino-acid and/or polyphosphazine segments, among others), and (c) mono-, di- and tri-functional alcohols having at least one polyisobutylene segment and at least one biodegradable polymeric segment. Commonly employed polymeric alcohols include macroglycols such as (a) polyisobutylene diols, (b) biodegradable polymer diols (e.g., biodegradable polyester diols, polycarbonate diols, polyorthoester diols, polyphosphazine diols, polyanhydride diols, poly(amino acid) diols, etc.), and (c) block copolymer diols having at least one polyisobutylene segment and at least one biodegradable polymeric segment.

In certain specific embodiments, the following may be employed in the formation of polyurethanes (a) a polymeric diol and (b) an aliphatic or aromatic monomeric diisocyanate. Optionally, monomeric aliphatic or aromatic diols or diamines may be employed as chain extenders in the copolymers of the invention, for example, to impart improved physical properties to the polyurethane. Where diamines are employed as chain extenders, urea linkages are formed and the resulting polymers may be referred to as polyurethane/polyureas.

Polyureas are a family of copolymers that comprise urea linkages,

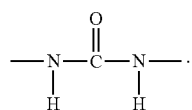

They may be synthesized from (a) mono- and poly-functional isocyanates, which may be monomeric or polymeric in nature and (b) mono- and poly-functional amines, which may monomeric or polymeric in nature.

Specific examples of monofunctional and multifunctional isocyanates are discussed above in conjunction with polyurethanes.

Specific examples of monofunctional and multifunctional monomeric amines include aliphatic and aromatic amines, for instance, selected from the diamines set forth below, among others. Specific examples of monofunctional and multifunctional polymeric amines include (a) mono-, di- and tri-functional amines having at least one polyisobutylene segment, (b) mono-, di- and tri-functional amines having at least one biodegradable polymeric segment (e.g., biodegradable polyester, polycarbonate, polyorthoester, polyanhydride, poly-amino-acid and/or polyphosphazine segments, among others), and (c) mono-, di- and tri-functional amines having at least one polyisobutylene segment and at least one biodegradable polymeric segment.

Commonly employed polymeric polyamines for use in conjunction with the present invention include polymeric diamines such as (a) polyisobutylene diamines, (b) biodegradable polymer diamines (e.g., biodegradable polyester diamines, polycarbonate diamines, polyorthoester diamines, polyphosphazine diamines, polyanhydride diamines, poly(amino acid) diamines, etc.), and (c) block copolymer diamines having at least one polyisobutylene segment and at least one biodegradable polymeric segment.

In certain specific embodiments, the following may be employed in the formation of polyureas: (a) a polymeric diamine (e.g., procedures suitable for forming polyisobutylene mono-amines and diamines are described in U. Ojha et al., *Macromolecules* 2008, 41, 3832-3841) and (b) an aliphatic or aromatic monomeric diisocyanate. Optionally, monomeric aliphatic or aromatic diol or diamine may be employed as chain extenders.

Polyamides (i.e., polymers that comprise amide linkages,

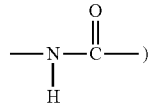

may be synthesized from (a) monofunctional or multifunctional amines (which may be monomeric or polymeric in nature) or monofunctional or multifunctional isocyanates (which may be monomeric or polymeric in nature), and (b) monofunctional or multifunctional carboxylic acids or acid chlorides (which may be monomeric or polymeric in nature). (Where isocyanates are reacted with carboxylic acids, $CO_2$ may be produced during the course of chemical reaction.)

Specific examples of monofunctional and multifunctional monomeric and polymeric amines and monofunctional and multifunctional monomeric and polymeric isocyanates are discussed above in conjunction with polyurethanes and polyureas.

Specific examples of polymeric monofunctional and multifunctional carboxylic acids and acid chlorides include (a) mono-, di- and tri-functional carboxylic acids and acid chlorides having at least one polyisobutylene segment, (b) mono-, di- and tri-functional carboxylic acids and acid chlorides comprising at least one biodegradable polymeric segment (e.g., biodegradable polyester, polycarbonate, polyorthoester, polyanhydride, poly-amino-acid and/or polyphosphazine segments, among others), and (c) mono-, di- and tri-functional carboxylic acids and acid chlorides having at least one polyisobutylene segment and at least one biodegradable polymeric segment. For instance, procedures suitable for forming polyisobutylene mono- and di-carboxylic acids are described in U. Ojha et al., *Macromolecules* 2008, 41, 3832-3841.

Specific examples of monomeric acids and acid chlorides include mono-, di- and tri-functional carboxylic acids and acid chlorides, specific examples of which include the dicarboxylic acids set forth hereinbelow and acid chloride versions of the same.

In a specific embodiment, the following may be employed in the formation of a polyamide: (a) a polymeric diamine or diisocyanate (e.g., one containing at least one polyisobutylene segment and at least one biodegradable polymeric segment), (b) a monomeric dicarboxylic acid or diacid chloride and (c) an optional chain extender, for example, a monomeric diamine or diisocyanate. In another specific embodiment, the following may be employed in the formation of a polyamide: (a) a monomeric diamine or diisocyanate, (b) a polymeric dicarboxylic acid or diacid chloride (e.g., one containing at least one polyisobutylene segment and at least one biodegradable polymeric segment) and (c) an optional chain extender, for example, a monomeric dicarboxylic acid or diacid chloride. In yet another specific embodiment, the following may be employed in the formation of a polyamide: (a) a polymeric diamine or diisocyanate (e.g., one containing at least one polyisobutylene segment), (b) a polymeric dicarboxylic acid or diacid chloride (e.g., one containing at least one biodegradable polymeric segment) and (c) an optional chain extender, for example, a monomeric diamine, diisocyanate, dicarboxylic acid and/or diacid chloride. In still another specific embodiment, the following may be employed in the formation of a polyamide: (a) a polymeric diamine or diisocyanate (e.g., one containing at least one biodegradable polymeric segment) (b) a polymeric dicarboxylic acid or diacid chloride (e.g., one containing at least one polyisobutylene segment) and (c) an optional chain extender, for example, a monomeric diamine, diisocyanate, dicarboxylic acid and/or diacid chloride.

Polyesters (i.e., polymers that comprise ester linkages) may be synthesized from (a) monofunctional or multifunctional alcohols (which may be monomeric or polymeric in nature) and (b) monofunctional or multifunctional carboxylic acids (which may be monomeric or polymeric in nature) or monofunctional or multifunctional acid chlorides (which may be monomeric or polymeric in nature). Specific examples of monofunctional and multifunctional monomeric and polymeric alcohols are discussed above in conjunction with polyurethanes. Specific examples of monofunctional and multifunctional monomeric and polymeric carboxylic acids and acid chlorides are discussed above in conjunction with polyamides.

In a specific embodiment, the following may be employed in the formation of a polyester: (a) a polymeric diol (e.g., one containing at least one polyisobutylene segment and at least one biodegradable polymeric segment), (b) a monomeric dicarboxylic acid or diacid chloride and (c) an optional chain extender, for example, a monomeric diol. In another specific embodiment, the following may be employed in the formation of a polyester: (a) a monomeric diol, (b) a polymeric dicarboxylic acid or diacid chloride (e.g., one containing at least one polyisobutylene segment and at least one biodegradable polymeric segment) and (c) an optional chain extender, for example, a monomeric dicarboxylic acid or diacid chloride. In yet another specific embodiment, the following may be employed in the formation of a polyester: (a) a polymeric diol (e.g., one containing at least one polyisobutylene segment), (b) a polymeric dicarboxylic acid or diacid chloride (e.g., one containing at least one biodegradable polymeric segment) and (c) an optional chain extender, for example, a monomeric diol, dicarboxylic acid and/or diacid chloride. In still another specific embodiment, the following may be employed in the formation of a polyester: (a) a polymeric diol (e.g., one containing at least one biodegradable polymeric segment) (b) a polymeric dicarboxylic acid or diacid chloride (e.g., one containing at least one polyisobutylene segment) and (c) an optional chain extender, for example, a monomeric diol, dicarboxylic acid and/or diacid chloride.

Polycarbonates (i.e., polymers that comprise carbonate linkages) may be synthesized from (a) phosgene and (b) monofunctional or multifunctional alcohols (which may be monomeric or polymeric in nature). Specific examples of monofunctional and multifunctional monomeric and polymeric alcohols are discussed above in conjunction with polyurethanes.

In a specific embodiment, the following may be employed in the formation of a polycarbonate: (a) phosgene (b) a polymeric diol containing at least one polyisobutylene segment and at least one biodegradable polymeric segment, and (c) an optional chain extender, for example, a monomeric diol. In another specific embodiment, the following may be employed in the formation of a polycarbonate: (a) phosgene, (b) a polymeric diol containing at least one polyisobutylene segment, (c) a polymeric diol containing at least one biodegradable polymeric segment, and (d) an optional chain extender, for example, a monomeric diol.

Polyanhydrides (i.e., polymers that comprise anhydrides linkages) may be synthesized from monofunctional or multifunctional carboxylic acids (which may be monomeric or polymeric in nature). Specific examples of monofunctional and multifunctional monomeric and polymeric carboxylic acids are discussed above in conjunction with polyamides.

In a specific embodiment, the following may be employed in the formation of a polyanhydride: (a) a polymeric dicarboxylic acid containing at least one polyisobutylene segment and at least one biodegradable polymeric segment and (b) an optional chain extender, for example, a monomeric dicarboxylic acid. In another specific embodiment, the following may be employed in the formation of a polyanhydride: (a) a polymeric dicarboxylic acid containing at least one polyisobutylene segment, (b) a polymeric dicarboxylic acid containing at least one biodegradable polymeric segment, and (c) an optional chain extender, for example, a monomeric dicarboxylic acid.

Polymers comprising linkages commonly described as "click" chemistry linkages may also be formed in accordance with the present invention. For example, linkages comprising a 1,2,3-triazole moiety may be formed by a cycloaddition reaction between (a) monofunctional or multifunctional azides (which may be monomeric or polymeric in nature) and (b) monofunctional or multifunctional alkynes (which may be monomeric or polymeric in nature).

Specific examples of monofunctional and multifunctional polymeric alkynes include (a) mono-, di- and tri-functional alkynes having at least one polyisobutylene segment, (b) mono-, di- and tri-functional alkynes having at least one biodegradable polymeric segment (e.g., biodegradable polyester, polycarbonate, polyorthoester, polyanhydride, polyamino-acid and/or polyphosphazine segments, among others), and (c) mono-, di- and tri-functional alkynes having at least one polyisobutylene segment and at least one biodegradable polymeric segment. For instance, procedures suitable for forming polyisobutylene mono- and di-alkynes are described in U. Ojha et al., *Macromolecules* 2008, 41, 3832-3841.

Specific examples of monofunctional and multifunctional polymeric azides include (a) mono-, di- and tri-functional azides having at least one polyisobutylene segment, (b) mono-, di- and tri-functional azides having at least one biodegradable polymeric segment (e.g., biodegradable polyester, polycarbonate, polyorthoester, polyanhydride, polyamino-acid and/or polyphosphazine segments, among others), and (c) mono-, di- and tri-functional azides having at least one polyisobutylene segment and at least one biodegradable polymeric segment. For instance, procedures suitable for forming polyisobutylene mono- and di-azides are described in U. Ojha et al., *Macromolecules* 2008, 41, 3832-3841.

In a specific embodiment, the following may be employed in the formation of a polymer with 1,2,3-triazole linkages: (a) a polymeric diazide (e.g., one containing at least one polyisobutylene segment and at least one biodegradable polymeric segment), (b) a monomeric dialkyne and (c) an optional chain extender, for example, a monomeric diazide. In another specific embodiment, the following may be employed in the formation of a polymer with 1,2,3-triazole linkages: (a) a monomeric diazide (b) a polymeric dialkyne (e.g., one containing at least one polyisobutylene segment and at least one biodegradable polymeric segment) and (c) an optional chain extender, for example, a monomeric dialkyne. In yet another specific embodiment, the following may be employed in the formation of a polymer with 1,2,3-triazole linkages: (a) a polymeric diazide (e.g., one containing at least one polyisobutylene segment), (b) a polymeric dialkyne (e.g., one containing at least one biodegradable polymeric segment) and (c) an optional chain extender, for example, a monomeric diazide and/or dialkyne. In still another specific embodiment, the following may be employed in the formation of a polymer with 1,2,3-triazole linkages: (a) a polymeric diazide (e.g., one containing at least one biodegradable polymeric segment), (b) a polymeric dialkyne (e.g., one containing at least one polyisobutylene segment) and (c) an optional chain extender, for example, a monomeric diazide or dialkyne.

Using the above and other strategies (a) a monofunctional polyisobutylene (PTB) may be coupled to a monofunctional biodegradable polymer (PDeg), yielding a PIB-PDeg diblock copolymer, (b) a monofunctional polyisobutylene may be coupled to a difunctional biodegradable polymer, yielding a PIB-PDeg-PIB triblock copolymer, (c) a difunctional polyisobutylene may be coupled to a monofunctional biodegradable polymer, yielding a PDeg-PIB-PDeg triblock copolymer, (d) difunctional polyisobutylene may be coupled to a difunctional biodegradable polymer, yielding a multiblock -PIB-PDeg-PIB-PDeg-copolymer, (e) a monofunctional polyisobutylene may be coupled to a tri-functional (or greater) biodegradable polymer, yielding a star copolymer, or (f) a tri-functional (or greater) polyisobutylene may be coupled to a monofunctional biodegradable polymer, yielding a star copolymer, among many other possibilities. As will be readily understood by those of ordinary skill in the art, diblock, triblock and star copolymer structures analogous to those in categories (a), (b), (c), (e) and (f) may also be formed by processes wherein a polymerization reaction is conducted in the presence of a suitable monofunctional, difunctional, trifunctional (or greater) macroinitiator. (For a specific example, see Example 1 below.) As seen from the polyurethane discussion below, the use of chain extenders commonly results in the formation of multiblock copolymers.

As previously noted, according to certain aspects of the invention, copolymers are provided, which contain: (a) one, two, three, four or more polyisobutylene segments, (b) one, two, three, four or more biodegradable polymer segments, and (c) zero, one, two, three, four or more optional segments, for example, segments containing one or more chain extender residues, among other possibilities.

The polyisobutylene segments can vary widely in molecular weight, for example, having number average molecular weights ($M_n$) ranging from 500 to 20,000, for example, from 500 to 750 to 1,000 to 1,500 to 2,000 to 2,500 to 5,000 to 7,500 to 10,000 to 15,000 to 20,000, among other values.

Examples of biodegradable polymer segments for use in the present invention may be selected from suitable members of the following, among others: (a) biodegradable polyester segments, including homopolymer and copolymer segments comprising one or more monomers selected from hydroxyacids such as glycolide, D-lactide, L-lactide, beta-hydroxybutyrate, beta-hydroxyvalerate, beta-malic acid, D-gluconate, L-gluconate, etc., and lactones such as epsilon-caprolactone and delta-valerolactone, etc., p-dioxanones (resulting in the formation of polyether esters), etc., for example, selected from the following segments: polyglycolide, poly-L-lactide (PLLA), poly-D-lactide, poly-D,L-lactide, poly(beta-hydroxybutyrate), poly-D-gluconate, poly-L-gluconate, poly-D,L-gluconate, poly(epsilon-caprolactone), poly(delta-valerolactone), poly(p-dioxanone), poly(lactide-co-glycolide) (PLGA), poly(lactide-co-delta-valerolactone), poly(lactide-co-epsilon-caprolactone), poly(lactide-co-beta-malic acid), and poly(beta-hydroxybutyrate-co-beta-hydroxyvalerate), among others, (b) biodegradable polycarbonate segments, including homopolymers and copolymer segments comprising one or more carbonate monomers selected from trimethylene carbonate, tetramethylene carbonate, 2,2-dimethyltrimethylene carbonate, etc., for example, selected from the following segments: poly(trimethylene carbonate), poly(tetramethylene carbonate), poly(2,2-dimethyltrimethylene carbonate), poly(lactide-co-trimethylene carbonate) and poly(glycolide-co-trimethylene carbonate), among others, (c) polyorthoester segments formed by the transesterification between a diol and diethoxytetrahydrofuran, for example, those formed by the reaction of diols such as trans-cyclohexanedimethanol (tCDM), 1,6-hexane diol (1,6-HD), 1,12-dodecane diol (1,12-DL) etc.) with diketene acetals such as 3,9-bis(ethylidene 2,4,8,10-tetraoxaspiro[5,5]undecane) (DETOSU), and those formed by the polymerization of a triol with an orthoester, (d) polyanhydride segments such as homopolymer and copolymer segments comprising one or more monomers selected from malonic acid, succinic acid, glutaric acid, pimelic acid, suberic acid, azelaic acid, sebacic acid (SA), maleic acid, isophthalic acid (ISO), hexadecandioic acid (HDA), fumaric acid (FA), terephthalic acid (TA), adipic acid (AA), dodecanedioic acid (DD), erucic acid dimer (EAD), and bis(p-carboxyphenoxy)alkanes such as bis(p-carboxyphenoxy)methane, bis(p-carboxyphenoxy) propane (CPP), and bis(p-carboxyphenoxy)hexane, for example, polyanhydride segments selected from the following: poly(adipic anhydride), poly(suberic anhydride), poly(sebacic anhydride), poly(dodecanedioic anhydride), poly(maleic anhydride), poly(sebacic acid-co-fumaric anhydride), poly[bis(p-carboxyphenoxy)methane anhydride], poly[1,3-bis(p-carboxyphenoxy)propane anhydride], poly[1,6-bis(p-carboxyphenoxy)hexane anhydride] and poly[1,3-bis(p-carboxyphenoxy)propane-co-sebacic acid anhydride], among others; (e) poly(phosphazine) segments, and (f) poly(amino acid) segments, including homopolymer and copolymer segments comprising naturally occurring amino acids such as alanine, arginine, asparagine, aspartic acid, cysteine, glutamic acid, glutamine, glycine, histidine, isoleucine, leucine, lysine, methionine, phenylalanine, proline, serine, threonine, tryptophan, tyrosine and valine, as well as atypical amino acids such as lanthionine, 2-aminoisobutyric acid, dehydroalanine and gamma-aminobutyric acid, as well as synthetic amino acid sequences, for example, amino acid derivatives such as those comprising γ-benzyl-$_L$-glutamate and ε-carbobenzoxy-L-lysine, for instance, a poly(γ-benzyl-$_L$-glutamate) (PBLG) segment or a poly(ε-carbobenzoxy-L-lysine) segment, segments comprising dimers based on a deaminated hydroxyl amino acid and an alkyl or aromatic ester of a hydroxyl amino acid, particularly desaminotyrosyl-tyrosine alkyl and aromatic esters (abbreviated as DTR, where R stands for the specific alkyl or aromatic ester used) such as desaminotyrosyl-tyrosine ethyl ester (DTE), desaminotyrosyl-tyrosine butyl ester (DTB), desaminotyrosyl-tyrosine hexyl ester (DTH), desaminotyrosyl-tyrosine octyl ester (DTO), desaminotyrosyl tyrosine dodecyl ester (DTD) and desaminotyrosyl tyrosine benzyl ester, for example, tyrosine-based polycarbonate segments (e.g., copolymers formed by the condensation polymerization of phosgene and a diphenol selected, for instance, from ethyl, butyl, hexyl, octyl, dodecyl, and bezyl esters of desaminotyrosyl-tyrosine, among others), tyrosine-based polyarylate segments (e.g., copolymers of a diphenol and a diacid linked by ester bonds, with diphenols selected, for instance, from ethyl, butyl, hexyl, octyl, dodecyl and bezyl esters of desaminotyrosyl-tyrosine, among others and diacids selected, for instance, from succinic, glutaric, adipic, suberic and sebacic acid, among others), and tyrosine-, leucine- and lysine-based polyester-amide segments, for example, comprising a combination of a desaminotyrosyl tyrosine alkyl or aromatic ester, desaminotyrosyl tyrosine, and various diacids, for example, succinic acid and adipic acid, among others.

The biodegradable polymer segments within the copolymers of the invention may be hard segments or soft segments. A few examples of biodegradable polymer segments with reported Tg values follow: (a) polyester segments such as poly(l-lactide) (Tg 60-65° C.), poly(d,l-lactide) (Tg 55-60° C.), poly(d,l-lactide-co-glycolide) (Tg 45-55° C.), poly(epsilon-caprolactone) (Tg −62° C.), poly(3-hydroxybutyrate) (Tg 1° C.), poly(3-hydroxybutyrate-co-3-hydroxyvalyrate) (Tg ~0° C.), poly(p-dioxanone) (Tg −10 to 0° C.), poly(ethylene carbonate) (T$_g$ 10 to 30° C.), and poly(trimethylene carbonate) (Tg −15° C.), (b) polyanhydride segments such as poly(CPP-ISO) (20:80) (Tg 110° C.), poly(CPP-ISO) (50:50) (Tg 100° C.), poly(CPP-ISO) (75:25) (Tg 230° C.), poly(CPP-ISO-SA) (15:58:27) (Tg 46° C.), poly(CPP-ISO-SA) (17:66:16) (Tg 83° C.), poly(CPP-ISO-TA) (50:40:10) (Tg 111.6° C.), poly(CPP-ISO-TA) (25:60:15) (Tg 105° C.), poly(EAD) (Tg<0° C.), poly(CPP-SA) (46:54) (Tg 1.6° C.), poly(EAD-SA) (22:78) (Tg<10° C.) and poly(EAD-SA) (8:92) (Tg<10° C.), and (c) polyorthoester segments such as poly(DETOSU-tCDM) (Tg 120° C.), poly(DETOSU-1,6-HD) (Tg ~20° C.), and poly(DETOSU-1,12-DL) (Tg ~0° C.).

Sources of Tg information include 1. Engelberg et al., *Biomaterials*, 12 (1991) 292-304, M. Zilberman et al., *Annu. Rev. Biomed. Eng.*, 8 (2006) 153-80, U.S. Pat. No. 4,997,904 to Domb, *Polymer Data Handbook*, James E. Mark, Ed., Oxford University Press, 1999, pp. 303-4 and 457-8, *Handbook of Biodegradable Polymers*, Abraham J. Domb, Joseph Kost, David M. Wiseman, Eds., CRC Press, 1997, Chapter 6, and *Scaffolding in Tissue Engineering*, Peter X. Ma and Jennifer Elisseeff, Eds., CRC Press, 2005, Chapter 7.

The biodegradable polymer segments in the copolymers of the invention may vary widely in molecular weight, for example, having a number average molecular weights ranging from 200 to 50,000, for example, from 200 to 500 to 1,000 to 2,500 to 5,000 to 10,000 to 25,000 to 50,000, among other values.

As indicated above, the various polymeric segments described herein, including polyisobutylene segments, biodegradable polymer segments, and combinations thereof, among others, can be incorporated into the copolymers of the invention by providing them in the form of mono- or multi-functional polymeric alcohols, isocyanates, amines, carboxylic acids, acid chlorides, alkynes, azides, and so forth, for example, by using them in the formation of urethane linkages, urea linkages, amide linkages, ester linkages, carbonate linkages, anhydride linkages, and linkages comprising a 1,2,3-triazole moiety, among others.

It should thus be clear that, while much of the discussion to follow is based on the use of mono- and multi-functional polymeric alcohols (typically polymeric diols) to form urethane linkages, methods may be performed using other mono- or multi-functional polymeric entities besides polymeric alcohols.

Specific examples of polyisobutylene polyols include linear polyisobutylene diols and branched (three-arm) polyisobutylene triols. See, e.g., J. P. Kennedy et al., "Designed Polymers by Carbocationic Macromolecular Engineering: Theory and Practice," Hanser Publishers 1991, pp. 191-193, Joseph P. Kennedy, *Journal of Elastomers and Plastics* 1985 17: 82-88, and the references cited therein. See also U. Ojha et al., *Macromolecules* 2008, 41, 3832-3841, wherein the synthesis of HO-Allyl-polyisobutylene-Allyl-OH diols are reported.

As previously indicated, in some embodiments, block copolymer polyols (e.g., diols, triols, etc.) are employed. Examples of such block copolymer polyols include block copolymer diols containing one or more polyisobutylene segments and one or more biodegradable polymer segments (e.g., biodegradable polyester, polycarbonate, polyorthoester, polyanhydride, polyphosphazine and/or poly(amino acid) segments, among others). Specific examples include diblock diols such as polyester-polyisobutylene diols, polycarbonate-polyisobutylene diols, polyorthoester-polyisobutylene diols, polyanhydride-polyisobutylene diols, polyphosphazine-polyisobutylene diols and poly(amino acid)-polyisobutylene diols, among others; triblock diols such as polyester-polyisobutylene-polyester diols, polycarbonate-polyisobutylene-polycarbonate diols, polyorthoester-polyisobutylene-polyorthoester diols, polyanhydride-polyisobutylene-polyanhydride diols, polyphosphazine-polyisobutylene-polyphosphazine diols, and poly(amino acid)-polyisobutylene-poly(amino acid) diols, among others; and so forth. As noted above, it is to be understood that analogous block copolymers in the form of diisocyanates, diamines, dicarboxylic acids, diacid chlorides, diazides and dialkynes, may be employed in the practice of the invention, among others.

As one specific example of a block copolymer polyol, among many others, HO-Allyl-polyisobutylene-Allyl-OH diols like those reported in U. Ojha et al., *Macromolecules* 2008, 41, 3832-3841, can be employed as a macroinitiator in the ring opening polymerization of L-lactide, resulting in the formation of a poly(L-lactide)-polyisobutylene-poly(L-lactide) triblock copolymer diol. See L. Sipos et al., *Macromol. Rapid Commun.* 2003, 16, 935-940.

Diisocyanates for use in forming copolymers in accordance with the invention, including polyurethanes, among other copolymers, include monomeric aromatic and non-aromatic (e.g., aliphatic) diisocyanates. Aromatic diisocyanates may be selected from suitable members of the following, among others: 4,4'-methylenediphenyl diisocyanate (MDI), 2,4- and/or 2,6-toluene diisocyanate (TDI), 1,5-naphthalene diisocyanate (NDI), para-phenylene diisocyanate, 3,3'-tolidene-4,4'-diisocyanate and 3,3'-dimethyl-diphenylmethane-4,4'-diisocyanate. Non-aromatic diisocyanates may be selected from suitable members of the following, among others: 1,6-hexamethylene diisocyanate (HDI), 4,4'-dicyclohexylmethane diisocyanate, 3-isocyanatomethyl-3,5,5-trimethylcyclohexyl isocyanate (isophorone diisocyanate or IPDI), cyclohexyl diisocyanate, and 2,2,4-trimethyl-1,6-hexamethylene diisocyanate (TMDI).

Optional chain extenders are typically aliphatic or aromatic diols (in which case a urethane bond is formed upon reaction with an isocyanate group) or aliphatic or aromatic diamines (in which case a urea bond is formed upon reaction with an isocyanate group). Chain extenders may be selected from suitable members of the following, among others: alpha,omega-alkane diols such as ethylene glycol (1,2-ethane diol), 1,3-propane diol, 1,4-butanediol, 1,5-pentanediol, 1,6-hexanediol, 1,8-octanediol, 1,9-nonanediol, 1,10-decanediol, and 1,12-dodacanediol, cyclic alkane diols such as 1,4-cyclohexane dimethanol, aromatic diols such as p-xyleneglycol and 1,4-bis(2-hydroxyethoxy) benzene, alpha,omega-alkane diamines, such as ethylene diamine, dibutylamine (1,4-butane diamine) and 1,6-hexanediamine, or 4,4'-methylene bis(2-chloroaniline).

As is known in the polyurethane art, in certain instances, chain extenders can be used to increase hard segment content (or, stated another way, can increase the ratio of hard segment material to soft segment material in the copolymer), which can in turn result in a polymer with higher modulus, lower elongation at break and increased strength.

As previously indicated, various synthetic strategies may be employed to create urethane copolymers in accordance with the invention. In certain embodiments, these strategies involve the reaction of the following: (a) one or more polyol (commonly a polymeric diol) species, (b) one or more polyisocyanate (commonly a monomeric diisocyanate) species as a chain extender, and (c) one or more optional species, such as monomeric diols or monomeric diamine species, as optional further chain extenders, if desired.

Urethane copolymers in accordance with the invention may the synthesized, for example, in bulk or using a suitable solvent (e.g., one capable or dissolving the various species that participate in the polymerization reaction).

In certain embodiments, a one step method may be employed in which (a) a macrodiol (M), for instance, a diblock diol such as one of those listed above (e.g., polyester-polyisobutylene diol, etc.) or a triblock diol such as one of those listed above (e.g., polyester-polyisobutylene-polyester diol, etc.) and (b) a diisocyanate (DI) (e.g., MDI, TDI, etc.) are reacted in a single step. Using this technique a polyurethane having alternating macrodiol and diisocyanate residues, i.e., -[DI-M-]$_n$, where n is an integer, is formed. In certain embodiments, a mixture of triblock diols with differing biodegradable blocks (e.g., a mixture of polylactide-polyisobutylene-polylactide diol and polycaprolactone-polyisobutylene-polycaprolactone diol, among many other possibilities) may be employed.

In some embodiments, a diol or diamine chain extender (CE) (e.g., 1,2-ethane diol, 1,4-butanediol, 1,6-hexanediol, etc.) is included in the reaction mixture. For example, where the ratio of M:CE:DI is 1:1:2, a polyurethane having the following idealized repeat structure may be formed, -[DI-M-DI-CE-]$_n$, although the M and CE residues may not be perfectly alternating as shown.

In other embodiments, a two-step reaction may be employed wherein the macrodiol (M) and diisocyanate (DI) are reacted in a first step to form diisocyanate-end-capped "prepolymers" DI-M-DI. Then, in a second step, a chain extender is added, along with additional diisocyanate, as required. For example, where the ratio of DI-M-DI:CE is 1:1, a polyurethane having the following repeat structure may be formed, -[DI-M-DI-CE-]$_n$. Due to enhanced reaction control, polyurethanes made by the two-step method may have a more regular structure than corresponding polyurethanes made by the one step method.

In certain other embodiments, a one step method may be employed in which a first macrodiol (M1) (e.g., a polyisobutylene diol), a second macrodiol (M2) (e.g., a biodegradable polymer diol such as a biodegradable polyester diol, polyorthoester diol, polyanhydride diol, poly(amino acid) diol, etc.) and a diisocyanate (DI) (e.g., MDI, TDI, etc.) are reacted in a single step. For example, where the ratio of M1:M2 is 1:1, a polyurethane having the following idealized repeat structure may be formed, -[DI-M1-DI-M2-]$_n$, although the chains may not be perfectly alternating as shown. In some embodiments, a chain extender (CE) may be added to the reaction mixture. For example, where the ratio of M1:M2:CE is 1:1:2, a polyurethane having the following idealized repeat structure may be formed, -[DI-M1-DI-CE-DI-M2-DI-CE-]$_n$, although the chains may not be perfectly alternating as shown.

In certain embodiments, a two-step method is employed in which first and second macrodiols (M1, M2) are independently reacted with diisocyanate in a first step to form isocyanate capped first and second prepolymers, for example DI-M1-DI and DI-M2-DI. In a second step, these prepolymers are reacted with a chain extender (CE), which reacts with the isocyanate end caps of the prepolymers. For example, where the ratio of DI-M1-DI:DI-M2-DI:CE is 1:1:2, a polyurethane having the following idealized repeat structure may be formed, -[DT-M1-DT-CE-DT-M2-DT-CE-]$_n$, although the chains may not be perfectly alternating as shown.

In some embodiments, a first macrodiol and a diisocyanate are reacted in a first step to form a first prepolymer, DI-M1-DI. This step is followed by second step in which the second macrodiol (M2) is added such that it reacts with one or both isocyanate end caps of the isocyanate capped first macrodiol. Depending on the relative ratios of DI-M1-DI and M2, this step may be used to create structures such as M2-DI-M1-DI and M2-DI-M1-DI-M2.

These structures can then be reacted with additional diisocyanate leading to chain extension. For example, a macrodiol prepolymer, M2-DI-M1-DI-M2, may be reacted with a diisocyanate (DI) to create structures along the following lines, -[M2-DI-M1-DI-M2-DI-]$_n$.

In certain embodiments, a macrodiol prepolymer, M2-DI-M1-DI-M2, is reacted with a chain extender (CE) a diisocyanate, as needed to maintain stoichiometry. For example, a chain extension process may be used to create idealized structures along the following lines, -[DI-M2-DI-M1-DI-M2-DI-CE-]$_n$, although it is again noted that the chains are not likely to be perfectly alternating as shown.

Thus, using techniques such as those above, among others, many possibilities exist whereby macrodiols (e.g. M, M1, M2, etc.), diisocyanates (DI), and optional chain extenders (CE) can be combined to produce copolymers in accordance with the invention.

As previously indicated analogous structure can be created using polymeric entities other than diols. As one example, in certain embodiments, a one step method may be employed in which (a) a macrodiamine (M), for instance, a diblock diamine (e.g., a poly(amino acid)-polyisobutylene diamine, etc.) or a triblock diamine (e.g., poly(amino acid)-polyisobutylene-poly(amino acid) diamine, etc.) and (b) a diisocyanate (DI) (e.g., MDI, TDI, etc.) are reacted in a single step. Using this technique a polyurea having alternating macrodiamine and diisocyanate residues, i.e., -[DI-M-]$_n$, where n is an integer, is formed.

Moreover, further reactions analogous to those above may be employed as well. For instance, in some embodiments, a diol or diamine chain extender (CE) is included in the reaction mixture. As another example, a combination of a poly(amino acid) macrodiamine and a polyisobutylene macrodiamine (M1,M2) may be employed, among many other possibilities.

In various embodiments, implantable and insertable medical devices are provided, which contain one or more polymeric regions containing one or more copolymers in accordance with various aspects of the invention. As used herein, a "polymeric region" is a region (e.g., an entire device, a device component, a device coating layer, etc.) that contains polymers, for example, from 50 wt % or less to 75 wt % to 90 wt % to 95 wt % to 97.5 wt % to 99 wt % or more polymers.

Examples of medical devices which can be provided in accordance with the invention vary widely and include medical devices for exterior application to the body such as patches for delivery of therapeutic agent to intact skin and broken skin (including wounds) and implantable or insertable medical devices, for example, stents (including coronary vascular stents, peripheral vascular stents, cerebral, urethral, ureteral, biliary, tracheal, gastrointestinal and esophageal stents), stent coverings, stent grafts, vascular grafts, abdominal aortic aneurysm (AAA) devices (e.g., AAA stents, AAA grafts, etc.), vascular access ports, dialysis ports, catheters (e.g., urological catheters or vascular catheters such as balloon catheters and various central venous catheters), guide wires, balloons, filters (e.g., vena cava filters and mesh filters for distal protection devices), embolization devices including cerebral aneurysm filler coils (including Guglielmi detachable coils and metal coils), embolic agents, tissue bulking devices, septal defect closure devices, drug depots that are adapted for placement in an artery for treatment of the portion of the artery distal to the device, myocardial plugs, patches, leads including pacemaker leads, defibrillation leads and coils, neurostimulation leads such as spinal cord stimulation leads, deep brain stimulation leads, peripheral nerve stimulation leads, cochlear implant leads and retinal implant leads, pulse generators, ventricular assist devices including left ventricular assist hearts and pumps, total artificial hearts, shunts, valves including heart valves and vascular valves, anastomosis clips and rings, cochlear implants, tympanostomy tubes, thoracic drainage tubes, nephrostomy tubes, and tissue engineering scaffolds for cartilage, bone, skin, nerve (e.g., for neural pathway regeneration, including the spinal cord,), and other in vivo tissue regeneration, sutures, suture anchors, tissue staples and ligating clips at surgical sites, cannulae, metal wire ligatures, urethral slings, hernia "meshes", artificial ligaments, tacks for ligament attachment and meniscal repair, joint prostheses, spinal discs and nuclei, orthopedic prosthesis such as bone grafts, bone plates, fins and fusion devices, orthopedic fixation devices such as interference screws in the ankle, knee, and hand areas, rods and pins for fracture fixation, screws and plates for craniomaxillofacial repair, dental implants, contact lenses, interocular lenses, punctum plugs, glaucoma shunts, or other devices that are implanted or inserted into the body.

In some embodiments, the polymeric regions of the present invention correspond to an entire medical device. In other embodiments, the polymeric regions correspond to one or more portions of a medical device. For instance, the polymeric regions can be in the form of medical device components, in the form of one or more fibers which are incorporated into a medical device, in the form of one or more polymeric layers formed over all or only a portion of an underlying substrate, and so forth. Materials for use as underlying medical device substrates include ceramic, metallic and polymeric substrates. Layers can be provided over an underlying substrate at a variety of locations and in a variety of shapes (e.g., in the form of a series of rectangles, stripes, or any other continuous or non-continuous pattern). As used herein a "layer" of a given material is a region of that material whose thickness is small compared to both its length and width. As used herein a layer need not be planar, for example, taking on the contours of an underlying substrate. Layers can be discontinuous (e.g., patterned).

In addition to one or more copolymers in accordance with the invention, polymeric regions for use in the medical devices may optionally contain one or more supplemental agents in some embodiments.

For example, in certain embodiments, one or more therapeutic agents are included beneath, within (e.g., blended with), or attached to (e.g., covalently or non-covalently bound to) polymeric regions in accordance with the invention. "Therapeutic agents," "drugs," "pharmaceutically active agents," "pharmaceutically active materials," and other related terms may be used interchangeably herein.

A wide variety of therapeutic agents can be employed in conjunction with the present invention including those used for the treatment of a wide variety of diseases and conditions (i.e., the prevention of a disease or condition, the reduction or elimination of symptoms associated with a disease or condition, or the substantial or complete elimination of a disease or condition).

Exemplary therapeutic agents for use in conjunction with the present invention include the following: (a) anti-thrombotic agents such as heparin, heparin derivatives, urokinase, clopidogrel, and PPack (dextrophenylalanine proline arginine chloromethylketone); (b) anti-inflammatory agents such as dexamethasone, prednisolone, corticosterone, budesonide, estrogen, sulfasalazine and mesalamine; (c) antineoplastic/antiproliferative/anti-miotic agents such as paclitaxel, 5-fluorouracil, cisplatin, vinblastine, vincristine, epothilones, endostatin, angiostatin, angiopeptin, monoclonal antibodies capable of blocking smooth muscle cell proliferation, and thymidine kinase inhibitors; (d) anesthetic agents such as lidocaine, bupivacaine and ropivacaine; (e) anti-coagulants such as D-Phe-Pro-Arg chloromethyl ketone, an RGD peptide-containing compound, heparin, hirudin, antithrombin compounds, platelet receptor antagonists, antithrombin antibodies, anti-platelet receptor antibodies, aspirin, prostaglandin inhibitors, platelet inhibitors and tick antiplatelet peptides; (f) vascular cell growth promoters such as growth factors, transcriptional activators, and translational promotors; (g) vascular cell growth inhibitors such as growth factor inhibitors, growth factor receptor antagonists, transcriptional repressors, translational repressors, replication inhibitors, inhibitory antibodies, antibodies directed against growth factors, bifunctional molecules consisting of a growth factor and a cytotoxin, bifunctional molecules consisting of an antibody and a cytotoxin; (h) protein kinase and tyrosine kinase inhibitors (e.g., tyrphostins, genistein, quinoxalines); (i) prostacyclin analogs; (j) cholesterol-lowering agents; (k) angiopoietins; (l) antimicrobial agents such as triclosan, cephalosporins, aminoglycosides and nitrofurantoin; (m) cytotoxic agents, cytostatic agents and cell proliferation affectors; (n) vasodilating agents; (o) agents that interfere with endogenous vasoactive mechanisms; (p) inhibitors of leukocyte recruitment, such as monoclonal antibodies; (q) cytokines; (r) hormones; (s) inhibitors of HSP 90 protein (i.e., Heat Shock Protein, which is a molecular chaperone or housekeeping protein and is needed for the stability and function of other client proteins/signal transduction proteins responsible for growth and survival of cells) including geldanamycin, (t) alpha receptor antagonist (such as doxazosin, Tamsulosin) and beta receptor agonists (such as dobutamine, salmeterol), beta receptor antagonist (such as atenolol, metaprolol, butoxamine), angiotensin-II receptor antagonists (such as losartan, valsartan, irbesartan, candesartan and telmisartan), and antispasmodic drugs (such as oxybutynin chloride, flavoxate, tolterodine, hyoscyamine sulfate, diclomine) (u) bARKct inhibitors, (v) phospholamban inhibitors, (w) Serca 2 gene/protein, (x) immune response modifiers including aminoquizolines, for instance, imidazoquinolines such as resiquimod and imiquimod, (y) human apolioproteins (e.g., AI, AII, AIII, AIV, AV, etc.), (z) selective estrogen receptor modulators (SERMs) such as raloxifene, lasofoxifene, arzoxifene, miproxifene, ospemifene, PKS 3741, MF 101 and SR 16234, (aa) PPAR agonists, including PPAR-alpha, gamma and delta agonists, such as rosiglitazone, pioglitazone, netoglitazone, fenofibrate, bexaotene, metaglidasen, rivoglitazone and tesaglitazar, (bb) prostaglandin E agonists, including PGE2 agonists, such as alprostadil or ONO 8815Ly, (cc) thrombin receptor activating peptide (TRAP), (dd) vasopeptidase inhibitors including benazepril, fosinopril, lisinopril, quinapril, ramipril, imidapril, delapril, moexipril and spirapril, (ee) thymosin beta 4, (ff) phospholipids including phosphorylcholine, phosphatidylinositol and phosphatidylcholine, (gg) VLA-4 antagonists and VCAM-1 antagonists, (hh) non-fouling, protein resistant agents such as polyethylene glycol and (ii) prohealing agents.

Numerous therapeutic agents, not necessarily exclusive of those listed above, have been identified as candidates for vascular treatment regimens, for example, as agents targeting restenosis (antirestenotics). Such agents are useful for the practice of the present invention and include one or more of the following: (a) Ca-channel blockers including benzothiazapines such as diltiazem and clentiazem, dihydropyridines such as nifedipine, amlodipine and nicardapine, and phenylalkylamines such as verapamil, (b) serotonin pathway modulators including: 5-HT antagonists such as ketanserin and naftidrofuryl, as well as 5-HT uptake inhibitors such as fluoxetine, (c) cyclic nucleotide pathway agents including phosphodiesterase inhibitors such as cilostazole and dipyridamole, adenylate/Guanylate cyclase stimulants such as forskolin, as well as adenosine analogs, (d) catecholamine modulators including α-antagonists such as prazosin and bunazosine, β-antagonists such as propranolol and α/β-antagonists such as labetalol and carvedilol, (e) endothelin receptor antagonists such as bosentan, sitaxsentan sodium, atrasentan, endonentan, (f) nitric oxide donors/releasing molecules including organic nitrates/nitrites such as nitroglycerin, isosorbide dinitrate and amyl nitrite, inorganic nitroso compounds such as sodium nitroprusside, sydnonimines such as molsidomine and linsidomine, nonoates such as diazenium diolates and NO adducts of alkanediamines, S-nitroso compounds including low molecular weight compounds (e.g., S-nitroso derivatives of captopril, glutathione and N-acctyl penicillamine) and high molecular weight compounds (e.g., S-nitroso derivatives of proteins, peptides, oligosaccharides, polysaccharides, synthetic polymers/oligomers and natural polymers/oligomers), as well as C-nitroso-compounds, 0-nitroso-compounds, N-nitroso-compounds and L-arginine, (g) Angiotensin Converting Enzyme (ACE) inhibitors such as cilazapril, fosinopril and enalapril, (h) ATII-receptor antagonists such as saralasin and losartin, (i) platelet adhesion inhibitors such as albumin and polyethylene oxide, (j) platelet aggregation inhibitors including cilostazole, aspirin and thienopyridine (ticlopidine, clopidogrel) and GP IIb/IIIa inhibitors such as abciximab, epitifibatide and tirofiban, (k) coagulation pathway modulators including heparinoids such as heparin, low molecular weight heparin, dextran sulfate and β-cyclodextrin tetradecasulfate, thrombin inhibitors such as hirudin, hirulog, PPACK (D-phe-L-propyl-L-arg-chloromethylketone) and argatroban, FXa inhibitors such as antistatin and TAP (tick anticoagulant peptide), Vitamin K inhibitors such as warfarin, as well as activated protein C, (l) cyclooxygenase pathway inhibitors such as aspirin, ibuprofen, flurbiprofen, indomethacin and sulfinpyrazone, (m) natural and synthetic corticosteroids such as dexamethasone, prednisolone, methprednisolone and hydrocortisone, (n) lipoxygenase pathway inhibitors such as nordihydroguairetic acid and caffeic acid, (o) leukotriene receptor antagonists, (p) antagonists of E- and P-selectins, (q) inhibitors of VCAM-1 and ICAM-1 interactions, (r) prostaglandins and analogs thereof including prostaglandins such as PGE1 and PGI2 and prostacyclin analogs such as ciprostene, epoprostenol, carbacyclin, iloprost and beraprost, (s) macrophage activation preventers including bisphosphonates, (t) HMG-CoA reductase inhibitors such as lovastatin, pravastatin, atorvastatin, fluvastatin, simvastatin and cerivastatin, (u) fish oils and omega-3-fatty acids, (v) free-radical scavengers/antioxidants such as probucol, vitamins C and E, ebselen, trans-retinoic acid SOD (orgotein) and SOD mimics, verteporfin, rostaporfin, AGI 1067, and M40419, (w) agents affecting various growth factors including FGF pathway agents such as bFGF antibodies and chimeric fusion proteins, PDGF receptor antagonists such as trapidil, IGF pathway agents including somatostatin analogs such as angiopeptin and ocreotide, TGF-β pathway agents such as polyanionic agents (heparin, fucoidin), decorin, and TGF-β antibodies, EGF pathway agents such as EGF antibodies, receptor antagonists and chimeric fusion proteins, TNF-α pathway agents such as thalidomide and analogs thereof, Thromboxane A2 (TXA2) pathway modulators such as sulotroban, vapiprost, dazoxiben and ridogrel, as well as protein tyrosine kinase inhibitors such as tyrphostin, genistein and quinoxaline derivatives, (x) matrix metalloprotease (MMP) pathway inhibitors such as marimastat, ilomastat, metastat, batimastat, pentosan polysulfate, rebimastat, incyclinide, apratastat, PG 116800, RO 1130830 or ABT 518, (y) cell motility inhibitors such as cytochalasin B, (z) antiproliferative/antineoplastic agents including antimetabolites such as purine analogs (e.g., 6-mercaptopurine or cladribine, which is a chlorinated purine nucleoside analog), pyrimidine analogs (e.g., cytarabine and 5-fluorouracil) and methotrexate, nitrogen mustards, alkyl sulfonates, ethylenimines, antibiotics (e.g., daunorubicin, doxorubicin), nitrosoureas, cisplatin, agents affecting microtubule dynamics (e.g., vinblastine, vincristine, colchicine, Epo D, paclitaxel and epothilone), caspase activators, proteasome inhibitors, angio genesis inhibitors (e.g., endostatin, angiostatin and squalamine), olimus family drugs (e.g., sirolimus, everolimus, tacrolimus, zotarolimus, etc.), cerivastatin, flavopiridol and suramin, (aa) matrix deposition/organization pathway inhibitors such as halofuginone or other quinazolinone derivatives, pirfenidone and tranilast, (bb) endothelialization facilitators such as VEGF and RGD peptide, (cc) blood rheology modulators such as pentoxifylline and (dd) glucose cross-link breakers such as alagebrium chloride (ALT-711).

Where a therapeutic agent is present, a range of loadings may be used in conjunction with the medical devices of the present invention. Typical therapeutic agent loadings range, for example, from than 1 wt % or less to 2 wt % to 5 wt % to 10 wt % to 25 wt % or more of the polymeric region.

Numerous techniques are available for forming polymeric regions in accordance with the present invention.

For example, where the copolymers of the invention have thermoplastic characteristics, a variety of thermoplastic processing techniques may be used to form polymeric regions from the same. Using these techniques, a polymeric region can be formed, for instance, by (a) first providing a melt that contains polymer(s) and any other optional agents such as therapeutic agents and (b) subsequently cooling the melt. Examples of thermoplastic processing techniques include compression molding, injection molding, blow molding, spraying, vacuum forming and calendaring, extrusion into sheets, fibers, rods, tubes and other cross-sectional profiles of various lengths, and combinations of these processes. Using these and other thermoplastic processing techniques, entire devices or portions thereof can be made.

Other processing techniques besides thermoplastic processing techniques may also be used to form polymeric regions in accordance with the present invention, including solvent-based techniques. Using these techniques, polymeric regions can be formed, for instance, by (a) first providing a solution or dispersion that contains polymer(s) and any optional supplemental agents such as therapeutic agents and (b) subsequently removing the solvent. The solvent that is ultimately selected will contain one or more solvent species, which are generally selected based on their ability to dissolve the polymer(s) that form the polymeric region, in addition to other factors, including drying rate, surface tension, etc. In certain embodiments, the solvent is selected based on its ability to dissolve or disperse the optional agents, if any. Thus, optional supplemental agents, such as therapeutic agents, may be dissolved or dispersed in the coating solution. Preferred solvent-based techniques include, but are not limited to, solvent casting techniques, spin coating techniques, web coating techniques, spraying techniques, dipping techniques, techniques involving coating via mechanical suspension including air suspension, ink jet techniques, electrostatic techniques, and combinations of these processes.

In some embodiments of the invention, a polymer containing solution (where solvent-based processing is employed) or a polymer containing melt (where thermoplastic processing is employed) is applied to a substrate to form a polymeric region. For example, the substrate can correspond to all or a portion of an implantable or insertable medical device to which a polymeric coating is applied, for example, by spraying, extrusion, and so forth. The substrate can also be, for example, a template, such as a mold, from which the polymeric region is removed after solidification. In other embodiments, for example, extrusion and co-extrusion techniques, one or more polymeric regions are formed without the aid of a substrate. In a specific example, an entire medical device is extruded. In another example, a polymeric coating layer is co-extruded along with and underlying medical device body. In another example, a polymeric region is extruded which is then assembled over a medical device substrate.

EXAMPLES

Below are examples of specific embodiments for carrying out the present invention. The examples are offered for illustrative purposes only, and are not intended to limit the scope of the present invention in any way.

Example 1

Synthesis of PLLA-b-PIB-b-PLLA

Six PLLA-b-PIB-b-PLLA triblock copolymers were synthesized with different PLLA and PIB segment lengths by ring-opening polymerization of L-lactide using HO-Allyl-PIB-Allyl-OH macroinitiators and tin octoate as the catalyst at 120° C. PIB diol macroinitiators with number average molecular weights ($M_n$) of 3400 (polydispersity index (PDI)=1.05) or 6700 (PDI=1.04) were synthesized by the hydrolysis of bromoallyl telechelic PIB with quantitative functional conversion as reported previously in U. Ojha et al., *Macromolecules* 2008, 41, 3832-3841.

A typical synthetic procedure for PLLA(350)-b-PIB(3400)-b-PLLA(350) is described as follows. HO-Allyl-PIB-Allyl-OH (2.0 g, 0.59 mmol) was placed in a two-necked round bottom flask fitted with a reflux condenser. The set up was kept under continuous nitrogen purging. The polymer was charged with 10 ml of dry toluene and stirred at room temperature to form a homogenous mixture. The solvent was then evaporated under reduced pressure. To the flask, L-lactide (419 mg, 2.95 mmol) was added and the mixture was kept under vacuum for 3 h at 50° C. The vacuum was released under nitrogen atmosphere and dry toluene (4 ml) was added to the mixture using a 10 mL glass syringe. A solution of stannous octoate (20 mg, 1 wt %) in 1 mL of dry toluene was added to the stirred solution using a 2 mL syringe and the mixture was heated at 120° C. for 24 h under nitrogen atmosphere. The solution was cooled to room temperature and poured into distilled methanol (25 mL) and kept undisturbed for 3 h. The supernatant liquid was decanted and the precipitate was separated. Further purification of the precipitate was carried out by dissolving it in chloroform (5 mL) at room temperature and adding the resulting solution to methanol (30 mL). The polymer was allowed to settle down. The liquid layer was removed and the polymer was repeatedly washed with excess methanol. The polymer was finally dried under vacuum overnight to remove the volatile impurities.

The six triblock copolymers with different hard block:soft block (HB:SB) compositions are described in Tables 1.

TABLE 1

The synthesis of PLLA-b-PIB-b-PLLA triblock copolymers

| Polymer PLLA/PIB/PLLA[3] | Code | PIB-[Allyl-OH]$_2$ (mmol)[1] | Yield (%) NMR/ Gravimetric[2] | L-lactide (mmol)[1] |
|---|---|---|---|---|
| 350/3400/350 | T3.34.3 | 1.18 | 100/87.2 | 5.9 |
| 710/3400/710 | T7.34.7 | 1.12 | 100/91.7 | 11.2 |
| 1800/3400/1800 | T18.34.18 | 1.20 | ~100/96.3 | 30.15 |
| 350/6700/350 | T3.67.3 | 0.57 | ~100/84.6 | 2.83 |
| 710/6700/710 | T7.67.7 | 0.59 | 100/98.0 | 5.9 |
| 1800/6700/1800 | T18.67.18 | 0.58 | ~100/92.4 | 14.5 |

[1]The molar equivalent of hydroxyallyl telechelic PIB and L-lactide used for the triblock copolymer synthesis,
[2]the gravimetric yield was calculated after purification of the polymers using precipitation method,
[3]the numbers given represent number average molecular weight for the various polymeric segments.

As seen from Table 2, the $M_n$ values from GPC and $^1$H NMR analysis were close to the theoretical value and indicated quantitative polymerization. The PDI values are also given in Table 2 for the precursor PIB macroinitiators and triblock copolymers.

TABLE 2

Molecular weight data of the precursor and triblock copolymers

| Polymer | PIB block ($M_n$)[1] | PDI | Weight % (PIB/PLLA)[2] | $M_n$[3] Theoretical | $M_n$[5] GPC | $M_n$[4] NMR | PDI[5] |
|---|---|---|---|---|---|---|---|
| T3.34.3 | 3400 | 1.10 | 83/17 | 4120 | 4500 | 4120 | 1.16 |
| T7.34.7 | 3400 | 1.10 | 70/30 | 4840 | 5100 | 4840 | 1.14 |
| T18.34.18 | 3400 | 1.10 | 49/51 | 7000 | 7400 | 7072 | 1.18 |
| T3.67.3 | 6700 | 1.07 | 90/10 | 7420 | 7500 | 7492 | 1.10 |
| T7.67.7 | 6700 | 1.07 | 82/18 | 8140 | 8500 | 8140 | 1.12 |
| T18.67.18 | 6700 | 1.07 | 65/35 | 10300 | 11300 | 10444 | 1.15 |

[1]molecular weight of hydroxyallyl telechelic PIB determined from GPC,
[2]represents the ratio of $M_{nPIB}$ to $M_{nPLLA}$,
[3]represents the designed molecular weight of PLLA-b-PIB-b-PLLA triblock copolymer,
[4]$M_n$ of the triblock copolymers determined from $^1$H NMR spectroscopic analysis,
[5]$M_n$ of the triblock copolymers determined from GPC analysis Example 2

Polyurethane Formation from PLLA-b-PIB-b-PLLA

The triblock copolymer diols formed in Example 1 were chain extended with MDI at elevated temperature in toluene in the presence of Sn(Oct)$_2$ to obtain the corresponding multiblock copolymers.

A typical chain extension of PLLA(350)-b-PIB(3400)-b-PLLA(350) is described as follows. PLLA(350)-b-PIB(3400)-b-PLLA(350) (1.45 g, 0.35 mmol) was dried by azeotropic distillation of dry toluene and kept under nitrogen at room temperature. To the polymer, 3 mL of dry toluene and stannous octoate (1 mol %) in toluene was added. The temperature was maintained at 75° C. To the stirred mixture, methyl-diphenyl-diisocyanate (MDI) (100 mg, 0.40 mmol) was added and stirring continued for 7 h. The solvent was evaporated at room temperature. The product was washed with hexanes repeatedly and dried under vacuum.

The $M_n$ values obtained with different MDI equivalents are listed in Table 3.

TABLE 3

Molecular weight and PDI of multiblock copolymers (PLLA(1800)-b-PIB(6700)-b-PLLA(1800) = 1 eq. and Sn(Oct)$_2$ = 1 mol % of triblock copolymer).

| MDI (equivalent) | $M_n$ (GPC-MALLS) | PDI | Yield[4] |
|---|---|---|---|
| Precursor copolymer | 10200 | 1.1 | 100 |
| 1.0[1] | 36000[3] | 1.4 | 91.5 |
| 1.10[1] | 51000[3] | 1.4 | 89.4 |
| 1.15[2] | 55600 | 1.3 | 93.0 |
| 2.0[1] | 38500[3] | 1.5 | 94.2 |

[1]GPC was recorded using chloroform as eluant,
[2]THF was used as the mobile phase,
[3]The GPC-RI traces showed bimodal molecular weight distribution,
[4]yields were calculated gravimetrically According to Table 3, the highest $M_n$ was obtained with 1.15 equivalent of MDI. This equivalent was used in all subsequent chain extensions.

The molecular weights and polydispersity indices of the multiblock copolymers are given in Table 4. The $M_n$ of the multiblock copolymers was obtained in the range of 43400-71400 with PDI=1.4-1.6.

TABLE 4

Molecular weight data of chain extended PLLA-b-PIB-b-PLLA triblock copolymers

| Polymer[1] | $M_n$ (GPC)[2] | PDI[5] | Yield[3] | Wt % (HB/SB)[4] |
|---|---|---|---|---|
| M18.67 | 71400 | 1.56 | 94.0 | 37/63 |
| M7.67 | 61600 | 1.50 | 92.0 | 20/80 |
| M3.67 | 64000 | 1.60 | 93.6 | 13/87 |
| M3.34 | 42400 | 1.53 | 86.0 | 22/78 |
| M7.34 | 49600 | 1.52 | 92.2 | 33/67 |
| M18.34 | 43400 | 1.40 | 96.4 | 52/48 |

[1]triblock copolymers were chain extended using MDI,
[2]samples were recorded using THF as the eluant,
[3]gravimetric yield of the polymers is reported,
[4]SB = soft segment, HB = hard segment, $M_{SB} = M_{PIB}$, $M_{HB} = M_{PLLA} + M_{MDI}$,
[5]PDI of the multiblock copolymers are derived from the GPC-RI traces.

All triblock and multiblock copolymers were soluble in tetrahydrofuran (THF), chloroform and dichloromethane (DCM) at room temperature. All triblock and multiblock copolymers (except M18.34) were soluble in toluene at room temperature.

Solution-cast samples were prepared by dissolving the polymer in chloroform (5 wt %). The solutions were centrifuged at 8000 rpm for 10 min and poured into a Teflon mold. The solvent was slowly evaporated at room temperature.

Compression molding of the polymers was carried out at 115° C. for 10 min at 3400 psi.

The DSC thermograms of the triblock and multiblock copolymers showed two glass transition temperatures ($T_g$) at ~−60° C. and ~45° C. in most of the cases (except T3.67 and its multi-block counterpart upon $1^{st}$ heating), indicating microphase separation. The as-synthesized multiblock copolymers showed a $T_m$ around 150° C. in the first heating scan (Table 5). Multiblock copolymers based on triblock copolymers with higher PLLA contents (T7.67, T18.67 and T18.34) showed a $T_m$ in both first and second heating scans although the enthalpy of melt transition on the second heating scan decreased compared to the first one.

Stress-strain measurements of PLLA-PIB multiblock copolymers revealed an increase in strength and Young's modulus (initial slope of the stress-strain curve) with increasing PLLA content.

Dynamic mechanical analysis (DMA) was used to determine various thermal transitions and mechanical stability of

TABLE 5

DSC data of the multiblock and triblock copolymers

| | $1^{st}$ heating[1] (° C.)[5] | | | $1^{st}$ heating[1] (° C.)[6] | | | | $2^{nd}$ heating[1] (° C.)[5] | |
| --- | --- | --- | --- | --- | --- | --- | --- | --- | --- |
| Polymer[3] | $T_{g1}$(PIB)[2] | $T_{g2}$(PLLA)[2] | $T_m$ | $T_{g1}$[2] | $T_{g2}$[2] | $T_{g1}$(PIB)[2] | $T_{g2}$(PLLA)[2] | $T_m$ | $T_c$[4] |
| 3.67 (M/T) | −63.1/−63.0 | — | 146.2/— | −64.5 | 27.3 | −64.2/−63.8 | 18.8/26.9 | — | — |
| 7.67 (M/T) | −62.5/−60.4 | 45.1/43.0 | 154.7/158.6 | −62.0 | 48.2 | −61.9/−62.5 | 40.4/41.8 | —/158.7 | —/109.3 |
| 18.67 (M/T) | −62.0/−63.1 | 46.9/48.1 | 161.0/147.0 | −59.9 | 46.8 | −60.8/−63.8 | 41.2/43.9 | 161/145.3 | 118.4/105.8 |
| 3.34 (M/T) | −60.3/−61.1 | 26.1/25.4 | 151.1/— | −61.3 | 32.1 | −60.9/−61.7 | 21.3/23.2 | — | — |
| 7.34 (M/T) | −58.9/−58.3 | 46.2/45.3 | 145.5/147.5 | −58.4 | 47.5 | −59.0/−60.4 | 38.1/36.3 | — | — |
| 18.34 (M/T) | −62.7/−57.1 | 48.5/55.0 | 145.1/155.1 | −59.2 | 50.7 | −62.7/−59.6 | 45.6/42.6 | —/156.6 | — |

[1]The samples were recorded at 10° C./min heating and cooling rate unless otherwise mentioned,
[2]$T_{g1}$ corresponded to the glass transition temperature of the PIB block and $T_{g2}$ corresponded to the glass transition temperature of the PLLA block,
[3]M/T represents the $T_g$ and $T_m$ of corresponding multiblock/triblock copolymer,
[4]represents the crystallization temperature,
[5]represents the first and second heating scans of as synthesized polymers,
[6]represents the first heating scan of chloroform-cast/compression-molded multiblock copolymers Table 6 gives the Young's modulus, ultimate stress and strain for as-synthesized compression molded films and chloroform-cast compression molded films.

The tensile stress of multiblock copolymers with less than 50 wt % PLLA varies between 8-11 MPa for PIB 3,400 and 6,700 segments. The M18.34 multiblock copolymer that contains 51 wt % PLLA exhibits greater strength (21 MPa). The ultimate strain values for the multiblock copolymers range from 100% to 400%.

M18.67 and M7.34 multiblock copolymers containing 34.6 wt % and 30 wt % PLLA have Young's modulus values of 25 MPa and 28 MPa respectively. M18.34 multiblock copolymer containing 51 wt % PLLA has a Young's modulus value of 42 MPa. Polymers containing ~17 wt % PLLA (M7.67 & M3.34) have much lower modulus values (~4 MPa). The multiblock copolymer containing 9.4 wt % PLLA has a modulus value of ~2 MPa.

the multiblock copolymers. The glass transition temperature (Tg) was obtained from the peak maximum of the tan delta curve. The values of storage modulus for the different films tested are listed in Table 6 along with the static tensile properties. A general declining trend of storage modulus for all the samples was observed with increasing temperature. A rapid reduction in storage modulus was observed at around −30° C., which corresponds to the glass transition of the soft segment (PIB). This was followed by a distinct rubbery plateau region for samples with relatively high content of PLLA (M7.34 and M18.34). They further showed a second rapid decrease in storage modulus at around 60° C., which corresponds to the glass transition temperature of the hard segment (PLLA).

TABLE 6

Mechanical properties of the multiblock copolymers processed under different conditions

| | | As-synthesized, Compression-mold[5] | | | | Chloroform-cast, Compression-mold[4,5] | |
| --- | --- | --- | --- | --- | --- | --- | --- |
| Polymer | PLLA wt % | Tensile stress (MPa)[1] | Tensile strain (%)[2] | Young's modulus (MPa)[6] | Storage modulus (MPa)[3] | Tensile stress (MPa)[1] | Tensile strain (%)[2] |
| M18.67 | 34.6 | 11 | 240 | 25 | 1.24 | 9.2 | 337 |
| M7.67 | 17.4 | 9 | 190 | 4 | 3.1 | 7.1 | 375 |
| M3.67 | 9.4 | 8 | 400 | 2 | 0.75 | 7.0 | 537 |
| M18.34 | 51 | 21 | 131 | 42 | 41.27 | 18.6 | 179 |
| M7.34 | 30 | 10 | 111 | 28 | 16.83 | 9.8 | 330 |
| M3.34 | 17.2 | 8 | 320 | 4 | 0.53 | 6.3 | 438 |

[1]represents the ultimate tensile strength at break,
[2]represents the maximum elongation at break,
[3]the storage modulus obtained from dynamic mechanical analysis at room temperature,
[4] 5% solution of the polymers were solvent-cast at room temperature,
[5] polymers were compression molded at 115° C. for 10 min,
[6] the Young's modulus is derived from the initial slope of the stress-strain curve.

AFM analysis of the multiblock copolymers showed phase segregation of hard and soft segment. In case of M18.67 (SB/HB=63/37, wt %) the spin-coated films show irregular phase segregation of the hard segment with an average diameter in the range of 7-10 nm. The spin-coated and annealed films of M18.34 (SB/HB=48/52, wt %) showed lamellar morphology and M3.67 (SB/HB=87/13, wt %) showed spherical morphology with the diameter of the hard segment domains in the range of 5-9 nm.

Example 3

Synthesis of PLLA-b-PIB-b-PLLA (PLLA Wt %≥60)

Triblock copolymers with PLLA wt %≈60-90 were synthesized by ring-opening polymerization of L-lactide using HO-Allyl-PIB-Allyl-OH ($M_n$=3300) as macroinitiator using a procedure described in Example 1.

The nomenclature and composition of the triblock copolymers are described in Table 7 below.

TABLE 7

PIB and PLLA wt % and Mn data of triblock copolymers

| Polymer | PIB($M_n$)/ PLLA($M_n$) | PLLA:PIB (wt %) | Theoretical‡ ($M_n$) | GPC ($M_n$) | PDI† |
|---|---|---|---|---|---|
| T26.34.26 | 3300/5200 | 61:39 | 8500 | 8100 | 1.2 |
| T66.34.66 | 3300/13200 | 80:20 | 15500 | 15200 | 1.2 |

The GPC $M_n$ data and NMR $M_n$ data (not shown) were close to the theoretical value as shown in Table 7 above and the polymers were obtained with quantitative conversion.

Example 4

Chain Extension of PLLA-b-PIB-b-PLLA (PLLA Wt %≥60)

The chain extension of above triblock copolymers in Example 3 were carried out with MDI at 75° C. as described in Example 2 (results are shown in Table 8).

TABLE 8

Molecular weight data of multiblock copolymers

| Polymer* | PIB($M_n$)/PLLA($M_n$) | HB:SB (wt %) | GPC ($M_n$) | PDI† |
|---|---|---|---|---|
| M26.34 | 3300/5200 | 62:38 | 53000 | 1.6 |
| M66.34 | 3300/13200 | 80:20 | — | — |

*The weight of MDI is added to HB,
†The PDI is determined from GPC analysis

The $T_g$ and $T_m$ data of the multiblock copolymers are listed in Table 9 below. All polymers showed a $T_m$ in the range of 141-170° C. The enthalpy of melt transition increased with the increase in PLLA content. All the polymers showed a $T_g$ in the range of 39-52° C. for the PLLA segment.

TABLE 9

The melting and glass transition temperatures of PLLA-PIB multiblock copolymers.

| Polymer | $T_g^1$ (° C.) | $T_m^1$ (° C.) | $\Delta H^1$ (J/g) | $T_g^2$ (° C.) | $T_m^2$ (° C.) | $\Delta H^2$ (J/g) |
|---|---|---|---|---|---|---|
| M66.34 | — | 170.78 | 51.65 | 52.24 | 161.9 | 35.01 |
| M26.34 | 49.3 | 141.62 | 21.20 | 39.24 | — | — |

[1]First scan (heating cycle),
[2]second scan (heating cycle).

The DMA data of the multiblock copolymers are described in Table 10. The storage moduli for the polymers were in the range of 2400-240 MPa. M26.34 (−32 and 52° C.) and M66.34 (−54 and 63° C.) each exhibited two $T_g$ values.

TABLE 10

Dynamic mechanical properties of PLLA-PIB multiblock copolymers.

| Polymer | Storage Modulus (MPa)* | $T_{g1}$ (° C.) | $T_{g2}$ (° C.) |
|---|---|---|---|
| M26.34 | 240 | −32 | 52 |
| M66.34 | 2,400 | −54 | 63 |

*Storage modulus value determined at 25° C.

The tensile properties of the multiblock copolymers are listed in Table 11. The Young's moduli of the multiblock copolymer were obtained in the range of 2.5-0.75 GPa with ultimate elongation at break≈2.5-18%.

TABLE 11

Static tensile properties of PLA-PIB multiblock copolymers.

| Polymer | PLA wt % | Young's modulus (GPa) | Tensile Stress (MPa) | Ultimate strain (%) |
|---|---|---|---|---|
| M26.34 | 60 | 0.75 | 23 | 18 |
| M66.34 | 80 | 2.5 | 17 | 2.5 |

Multiblock copolymers with PLLA ≥90 wt % were also synthesized but they were too brittle and test specimens could not be obtained.

Example 5

Synthesis of Poly(γ-Benzyl-$_L$-Glutamate) (PBLG)-b-PIB-b-PBLG

The synthesis of PBLG-b-PIB-b-PBLG triblock copolymer ($M_n$=4,770, PDI=1.12) was synthesized by ring-opening polymerization of γ-benzyl-$_L$-glutamate N-carboxyanhydride (Glu-NCA) using $NH_2$-Allyl-PIB-Allyl-$NH_2$ (PIB diamine) macroinitiators. A PIB diamine macroinitiator with $M_n$=2,390 and PDI=1.09 was synthesized by the hydrazinolysis of α,ω-phthalimide-functional PIB obtained in the reaction of α,ω-chloroallyl functional PIB and potassium phthalimide as reported previously in U. Ojha et al., *Macromolecules* 2008, 41, 3832-3841. Both conventional amine polymerization (*Biomacromolecules*, 5(5), 1653, 2004) and ammonium-mediated polymerization (*Chem. Commun.* 23, 2944, 2003) of Glu-NCA were carried out. The ammonium-mediated polymerization of Glu-NCA, described below, provided better control of molecular weights and lower PDIs compared to the conventional amine polymerization.

In particular, a glass apparatus, α,ω-amino-functional PIB (0.41 g, 0.176 mmol) was dissolved in dry THF (5 mL) under argon, and then acetic acid (0.10 g, 1.76 mmol) was added. After stirring for 10 min at room temperature, dry toluene (30 mL) was placed in the apparatus. The mixed solvents were distilled out together with excess acetic acid on a high vacuum line. The dry toluene (30 mL) was again added and azeotropically distilled to remove a trace of water. The resulting α,ω-ammonium-functional PIB was obtained by drying overnight under high vacuum condition ($10^{-6}$ Torr). The polymer was then redissolved in dry THF (11.5 mL). To this solution, Glu-NCA (0.51 g, 1.94 mmol) and dry DMF (5.0 mL) were added under high vacuum. The polymerization system was stirred at 60° C. for 4 days. The solution was taken out from the apparatus and then THF was evaporated under the reduced pressure. The concentrated DMF solution was poured in cold methanol (100 mL) to precipitate the polymer. It was filtered and dried under vacuum for 24 h to afford a white solid. Yield: 0.710 g, 85%.

Example 6

Chain Extension of PBLG-b-PIB-b-PBLG

In a 100 mL three neck round bottom flask, dry PBLG-b-PIB-b-PBLG (0.18 g, 0.0.383 mmol) was dissolved in dry THF/DMF (4 mL/1 mL) under nitrogen. The solution was heated to 40° C. and MDI (9.6 mg, 0.0384 mmol) was added. Following the reaction by FT-IR, the solution was stirred for 24 h at 40° C. The solution was concentrated under reduced pressure, and then poured in cold methanol (20 mL) to precipitate the polymer. It was filtered and dried under vacuum for 24 h to afford the $(ABA)_n$ multiblock copolymer ($M_n$=28500, PDI=2.8) as a white solid. Yield: 0.120 g, 67%.

Although various embodiments are specifically illustrated and described herein, it will be appreciated that modifications and variations of the present invention are covered by the above teachings and are within the purview of the appended claims without departing from the spirit and intended scope of the invention.

The invention claimed is:

1. A medical article, comprising:
a tubular member including a polymeric region, the polymeric region including a copolymer comprising a plurality of polyisobutylene segments having a number average molecular weight of 20,000 or less and a plurality of hard biodegradable polymer segments; and
wherein the copolymer includes one or more linkages comprising a 1,2,3-triazole moiety.

2. The medical article of claim 1, wherein the hard segments comprise a plurality of diisocyanate residues, a plurality of urethane linkages, a plurality of urea linkages, or a combination thereof.

3. The medical article of claim 1, wherein the hard segments comprise a plurality of diisocyanate residues and wherein the diisocyanate residues comprise non-aromatic diisocyanate residues.

4. The medical article of claim 1, wherein the hard segments comprise a plurality of diisocyanate residues wherein the diisocyanate residues comprise aromatic diisocyanate residues.

5. The medical article of claim 1, wherein the hard segments comprise a plurality of diisocyanate residues wherein the diisocyanate residues comprise residues of an aromatic diisocyanate selected from 4,4'-methylenediphenyl diisocyanate, toluene diisocyanate, 1,5-naphthalene diisocyanate, para-phenylene diisocyanate, 3,3'-tolidene-4,4'diisocyanate, 3,3'-dimethyl-diphenylmethane-4,4'-diisocyanate, and combinations thereof.

6. The medical article of claim 1, further comprising a plurality of chain extender residues.

7. The medical article of claim 6, wherein the chain extender residues are selected from aliphatic diol residues, aromatic diol residues, aliphatic diamine residues and aromatic diamine residues.

8. The medical article of claim 6, wherein the chain extender residues are selected from alpha,omega-C 1-C 10-alkane diol residues.

9. The medical article of claim 1, comprising from 2 to 50 polyisobutylene segments.

10. The medical article of claim 1, comprising from 2 to 50 biodegradable polymer segments.

11. The medical article of claim 1, wherein the tubular member is a stent, a catheter, a lead, an orthopedic screw, a suture, a venous valve, a cardiac valve, a graft, an aneurysm coil, an adhesion prevention coating, a pelvic mesh, a hernia mesh, or a spinal disc replacement.

12. The medical article of claim 1, wherein the polymeric region further comprises a therapeutic agent.

13. The medical article of claim 12, wherein the therapeutic agent is an antirestenotic agent.

14. An implantable medical devices, comprising:
a stent having a polymeric region, the polymeric region including a copolymer comprising a plurality of polyisobutylene segments having a number average molecular weight of 20,000 or less and a plurality of hard biodegradable polymer segments; and
wherein the copolymer includes one or more linkages comprising a 1,2,3-triazole moiety.

* * * * *